(12) United States Patent
Gentry et al.

(10) Patent No.: US 7,652,581 B2
(45) Date of Patent: Jan. 26, 2010

(54) METHOD AND SYSTEM FOR INTEGRATING A PASSIVE SENSOR ARRAY WITH A MATTRESS FOR PATIENT MONITORING

(75) Inventors: Jason M. Gentry, Berkeley, CA (US); Matthew S. Glei, Honolulu, HI (US); Scott A. Christensen, Danville, CA (US)

(73) Assignee: Hoana Medical, Inc., Honolulu, HI (US)

( * ) Notice: Subject to any disclaimer, the term of this patent is extended or adjusted under 35 U.S.C. 154(b) by 336 days.

(21) Appl. No.: 11/061,213

(22) Filed: Feb. 18, 2005

(65) Prior Publication Data

US 2005/0190068 A1 Sep. 1, 2005

Related U.S. Application Data

(60) Provisional application No. 60/546,695, filed on Feb. 18, 2004.

(51) Int. Cl.
*G08B 23/00* (2006.01)
(52) U.S. Cl. .................................. 340/573.1
(58) Field of Classification Search ............. 340/573.1, 340/539.12, 665; 600/300, 301, 481, 534, 600/435; 128/671
See application file for complete search history.

(56) References Cited

U.S. PATENT DOCUMENTS

| | | | |
|---|---|---|---|
| 3,898,981 A | 8/1975 | Basham | 128/2 R |
| 3,926,177 A | 12/1975 | Hardway, Jr. et al. | 128/2 S |
| 4,245,651 A | 1/1981 | Frost | 128/721 |
| 4,320,766 A | 3/1982 | Alihanka et al. | 128/671 |
| 4,359,726 A | 11/1982 | Lewiner et al. | 340/666 |
| 4,381,788 A | 5/1983 | Douglas | 128/722 |
| 4,539,560 A | 9/1985 | Fleck et al. | 340/573 |
| 4,562,723 A | 1/1986 | Hubner | 73/23 |
| 4,633,237 A | 12/1986 | Tucknott et al. | 340/573 |
| 4,657,026 A | 4/1987 | Tagg | 128/721 |
| 4,659,090 A * | 4/1987 | Kustanovich | 273/376 |
| 4,827,763 A | 5/1989 | Bourland et al. | 73/172 |
| 4,862,144 A | 8/1989 | Tao | 340/573 |
| 4,907,845 A | 3/1990 | Wood | 340/573 |
| 4,926,866 A | 5/1990 | Lee | 128/630 |
| 5,002,060 A | 3/1991 | Nedivi | 128/671 |
| 5,144,284 A | 9/1992 | Hammett | 340/573 |
| 5,271,412 A * | 12/1993 | Shtalryd et al. | 600/534 |
| 5,292,340 A | 3/1994 | Crosby et al. | 607/17 |
| 5,353,012 A | 10/1994 | Barham et al. | 340/573 |
| 5,448,996 A | 9/1995 | Bellin et al. | 128/671 |
| 5,459,452 A | 10/1995 | DePonte | 340/604 |

(Continued)

FOREIGN PATENT DOCUMENTS

GB 2350681 6/2000

(Continued)

*Primary Examiner*—Phung Nguyen
(74) *Attorney, Agent, or Firm*—Fulwider Patton LLP

(57) ABSTRACT

A system is provided for integrating a passive sensor or sensor array into a patient's mattress to support continuous passive monitoring of a patients' physiological conditions in a hospital setting. The sensor or sensor array may be incorporated into the mattress by fixing it to a coverlet that surrounds the mattress, or by embedding it within the mattress core. Alternatively, the sensor or sensor array may be fixed to an underlayer positioned between the mattress core and the coverlet.

64 Claims, 11 Drawing Sheets

U.S. PATENT DOCUMENTS

| | | | | |
|---|---|---|---|---|
| 5,590,650 | A | * | 1/1997 | Genova .................... 600/301 |
| 5,638,593 | A | | 6/1997 | Gerhardt et al. |
| 5,724,990 | A | | 3/1998 | Ogino .................... 128/782 |
| 5,808,552 | A | * | 9/1998 | Wiley et al. ............. 340/573.4 |
| 5,844,488 | A | | 12/1998 | Musick .................... 340/573 |
| 5,846,206 | A | | 12/1998 | Bader .................... 600/534 |
| 5,853,005 | A | | 12/1998 | Scanlon ................ 128/662.03 |
| 5,942,979 | A | | 8/1999 | Luppino .................... 340/576 |
| 5,964,720 | A | * | 10/1999 | Pelz .................... 600/595 |
| 5,989,193 | A | | 11/1999 | Sullivan .................... 600/534 |
| 5,991,949 | A | * | 11/1999 | Miller et al. .................... 5/710 |
| 6,025,782 | A | * | 2/2000 | Newham ................ 340/573.1 |
| 6,047,203 | A | | 4/2000 | Sackner et al. ............. 600/388 |
| 6,050,940 | A | | 4/2000 | Braun et al. .................... 600/300 |
| 6,146,332 | A | | 11/2000 | Pinsonneault et al. ....... 600/534 |
| 6,195,008 | B1 | | 2/2001 | Bader .................... 340/573.1 |
| 6,198,394 | B1 | | 3/2001 | Jacobsen et al. ......... 340/573.1 |
| 6,248,064 | B1 | | 6/2001 | Gopinathan et al. ......... 600/300 |
| 6,261,237 | B1 | | 7/2001 | Swanson et al. ............. 600/527 |
| 6,315,719 | B1 | | 11/2001 | Rode et al. .................. 600/300 |
| 6,375,621 | B1 | | 4/2002 | Sullivan .................... 600/484 |
| 6,377,177 | B1 | | 4/2002 | Broussard et al. ........... 340/687 |
| 6,402,691 | B1 | | 6/2002 | Peddicord et al. ........... 600/300 |
| 6,407,669 | B1 | * | 6/2002 | Brown et al. ............. 340/572.1 |
| 6,417,777 | B2 | | 7/2002 | Fitzgerald et al. ........ 340/573.1 |
| 6,445,299 | B1 | | 9/2002 | Rojas, Jr. .................. 340/573.1 |
| 6,450,957 | B1 | * | 9/2002 | Yoshimi et al. ............. 600/309 |
| 6,485,441 | B2 | | 11/2002 | Woodward .................. 600/595 |
| 6,497,658 | B2 | | 12/2002 | Roizen et al. ............... 600/301 |
| 6,506,153 | B1 | | 1/2003 | Littek et al. .................. 600/301 |
| 6,532,608 | B2 | | 3/2003 | Schreiner ....................... 5/497 |
| 6,547,743 | B2 | | 4/2003 | Brydon .................... 600/534 |
| 6,575,902 | B1 | | 6/2003 | Burton ....................... 600/300 |
| 6,754,516 | B2 | | 6/2004 | Mannheimer ............... 600/323 |
| 6,778,090 | B2 | | 8/2004 | Newham .................. 340/573.1 |
| 6,840,117 | B2 | | 1/2005 | Hubbard, Jr. ........... 73/862.041 |
| 6,840,907 | B1 | * | 1/2005 | Brydon ........................ 600/534 |
| 6,847,301 | B1 | | 1/2005 | Olson ........................ 340/666 |
| 6,984,207 | B1 | * | 1/2006 | Sullivan et al. ............. 600/301 |
| 6,988,989 | B2 | | 1/2006 | Weiner et al. ............... 600/300 |
| 7,304,580 | B2 | * | 12/2007 | Sullivan et al. .......... 340/573.1 |
| 2002/0193707 | A1 | | 12/2002 | Atlas et al. |
| 2004/0111045 | A1 | | 6/2004 | Sullivan et al. ............. 600/595 |
| 2004/0148706 | A1 | * | 8/2004 | Visser et al. .................... 5/720 |
| 2005/0190062 | A1 | * | 9/2005 | Sullivan et al. .......... 340/573.1 |
| 2006/0063982 | A1 | | 3/2006 | Sullivan et al. ............. 600/301 |

FOREIGN PATENT DOCUMENTS

| | | |
|---|---|---|
| JP | 10229973 | 9/1998 |
| WO | 01/64103 | 9/2001 |
| WO | WO 01/78601 A1 | 10/2001 |
| WO | 03/082111 | 10/2003 |
| WO | WO 03/082111 | 10/2003 |
| WO | 2005/000108 | 1/2005 |

* cited by examiner

METHOD AND SYSTEM FOR INTEGRATING A PASSIVE SENSOR ARRAY WITH A MATTRESS FOR PATIENT MONITORING

This application claims the benefit of provisional application Ser. No. 60/546,695, filed Feb. 18, 2004.

BACKGROUND OF THE INVENTION

1. Field of the Invention

The present invention relates generally to medical monitors and more specifically to a medical monitoring system for providing an invisible "safety net" for a patient that will observe and analyze the physiological parameters of a patient, and, in the event of a clinically significant negative condition, notify and report the event to the care staff utilizing the existing nurse call system of a hospital. Specifically the invention is directed to methods and systems for integrating a passive sensor array for such a system into a medical mattress used by a patient.

2. General Background and State of the Art:

Monitoring patients is an important aspect of patient care in many different settings. In a general care floor or ward of a hospital, for example, monitoring vital physiological signs such as respiratory rate, heart rate and blood pressure is a basic component of patient care. Monitoring the presence or absence of a patient in a hospital bed and monitoring patient movement on that bed may also be beneficial in a general care ward or other areas of a hospital. If certain patients leave their beds, they run a risk of falling and/or injuring themselves. If a patient stops moving in bed, it may mean that the patient is dying, is in a coma or is suffering from a medical complication that makes movement difficult or impossible and requires attention. Excessive movement may indicate a seizure or other condition.

Current systems for patient monitoring do not generally provide for convenient, constant, around-the-clock monitoring. On a general care ward of a hospital, for example, monitoring typically consists of a team of nurses circulating from patient to patient, at three- or four-hour intervals, to take vital signs such as respiratory rate and heart rate. In some hospitals, this monitoring may be augmented by one or more devices, such as a bedside pulse-oximeter, which monitors pulse and oxygen saturation via a small clamp-like device attached to a patient's finger. The pulse-oximeter may be designed to sound an alarm, if a certain pulse or oxygen threshold level is reached.

The currently available systems and methods for patient monitoring have several characteristics in common. Virtually all require a patient to be physically connected to a monitor apparatus. Many, such as automatic blood pressure cuffs, provide only for intermittent monitoring. Physical connection to monitoring apparatus can be cumbersome and inconvenient for patients, sometimes leading to patient noncompliance, such as when a patient removes a device due to discomfort. Attached devices may also loosen, change position, fall partially off the patient and the like, leading to inaccurate monitoring data. Intermittent monitoring can lead to missed or late diagnosis and adverse patient outcomes, especially in very sick patients whose conditions may change rapidly.

Currently available systems generally do not monitor patient movement or positioning. As described above, patient movement can be an essential monitoring tool. For example, complete absence of patient movement on a bed could indicate that the patient has left the bed. Relatively slight movement, a significant reduction in movement or the like could indicate that the patient is sufficiently still that some medical problem might have occurred. Significant increases in patient movement might indicate a seizure or significant patient discomfort.

Thus, efforts have been made to develop passive monitoring systems with sensors that are effectively "invisible" to the patient, i.e., hidden within the bedding or in the bed clothes used by a patient, where they may passively monitor the patient's physiological conditions and movement without the patient or hospital staff being aware of their presence. However, one of the challenges is how to mount the sensor to the bed in a way that does not degrade the properties of the original mattress or sleep surface, that is thin and comfortable for the patient, that is held securely in place on the mattress, does not crumple, fold, crease or bunch up, is cleanable using typical disinfecting agents used on healthcare mattresses, does not significantly attenuate or degrade the passive sensor electronic signal, fits mattresses of different manufacturers, sizes and materials, and does not affect the typical hospital workflow in making or changing the bedding.

The present invention addresses these needs.

SUMMARY OF THE INVENTION

Briefly, in general terms, the present invention provides a new and improved method and system for integrating a passive sensor or sensor array into a patient's mattress to support continuous passive monitoring of a patients' physiological conditions in a hospital setting. "Passive monitoring" generally refers to the fact that monitoring according to the invention does not require direct attachment of a device to a patient. Rather, a patient is coupled with a sensor device by simply allowing the patient lie, or sit, on the surface of a hospital bed.

In particular, the present invention provides a thin comfortable sensor pad or carrier sheet which can be securely integrated with the mattress assembly of a patient's hospital bed, and which will maintain the desirable properties of the patient's mattress assembly while allowing hospital personnel to change the bedding or clean the mattress without undue interference.

The pad or carrier sheet of the present invention can be mounted to the top or bottom side of the mattress assembly, as desired. It can be integrated within a mattress coverlet that fits over the original coverlet, or alternatively, can be used to replace the existing coverlet. It can be integrated into a replacement, additional, or existing underlayer disposed between the coverlet and the mattress assembly core. It also can be placed into the existing mattress assembly core, or integrated into a new replacement core.

In a preferred embodiment, the sensor device of the present invention includes an array of piezoelectric sensing elements and/or pressure switches mounted in a flat pad or carrier sheet, positioned on or within the mattress assembly of a hospital bed integrated with the sleep surface. In that location, the sensor is capable of monitoring the patient through one or more layers of bedding or patient clothing, or the like. The sensor is typically coupled to a processor, either by wired or wireless communication. The processor receives sensed data from the sensors and processes that sensed data into a form that is usable by a physician, nurse or other user. Any suitable patient parameter may be monitored, such as but not limited to patient movement, patient position, respiratory rate, heart rate, blood pressure and/or the like.

The sensor pad or carrier sheet may include any suitable number of sensors. Specifically, any number, pattern, size, shape or type of sensors is contemplated. Where more than two sensors are included in the sensor device, any combination of sensors may be used to sense signals and any combination of signals from various sensors may be compared to provide patient data to a user.

The piezoelectric sensors may be fabricated from any suitable material. However, in a preferred embodiment, the sensors are made of polyvinylidene fluoride film or other polarized polymer film with piezoelectric properties.

In some embodiments, the sensors may be embedded in a layer of resilient foam in the form of a pad suitable for enabling monitoring of a patient. In a preferred embodiment, the sensor array is mounted on the surface of a thin carrier sheet. The surface of the pad or carrier sheet may have any suitable dimensions. Preferably, the dimensions are sufficient to allow the pad or carrier sheet, and thus the sensor array, to extend across a substantial portion of the mattress surface between the patient's shoulder and buttocks.

Optionally, the sensor pad or carrier sheet may further include a protective layer disposed between the surface of the pad and the patient. Typically, such a protective layer will be water resistant.

Other features and advantages will become apparent from the following detailed description, taken in conjunction with the accompanying drawings, which illustrate, by way of example, the features of the present invention.

DETAILED DESCRIPTION OF THE PREFERRED EMBODIMENTS

Figure 1:
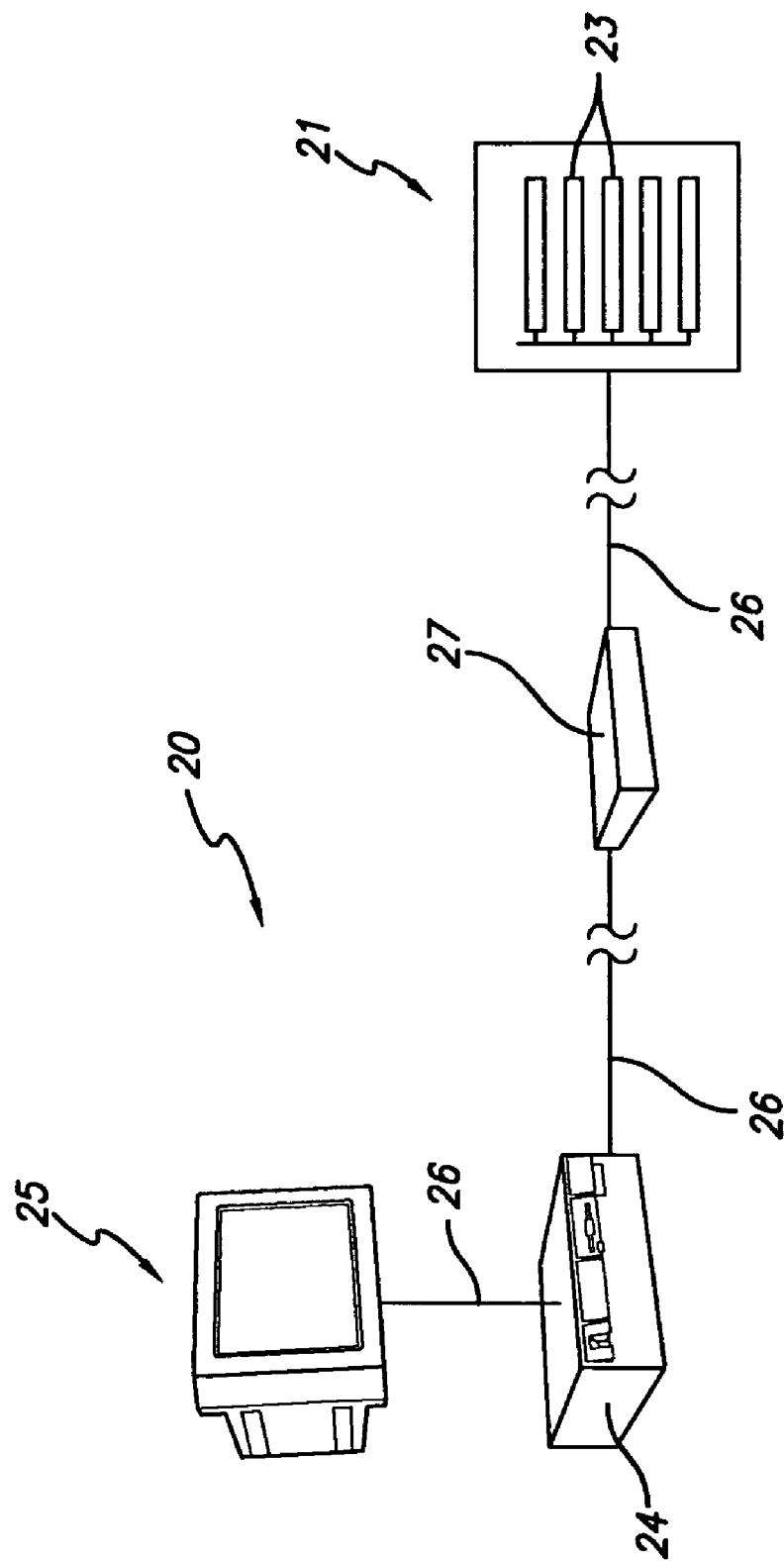
FIG. 1 is a schematic view of a system for passive patient monitoring, showing the relationship between an array of sensors, an anchor box, a processor, and a display device.

As shown in the drawings, which are provided for purposes of exemplary illustration, the invention is embodied in a variety of methods for mounting or integrating a passive sensor array, to be used for medical monitoring, onto or into a mattress assembly in a hospital or other healthcare facility.

Referring more specifically to FIG. 1, there is shown a generalized system 20 for passive patient monitoring including a sensor device 21 having at least two piezoelectric sensors 23, coupled with a processor 24, which is in turn coupled with a data display device 25 for providing physiological data to a user. Generally, the sensor device 21 may be coupled with the processor 24 via any suitable connector 26 (or multiple connectors), such as a cable, wire, wireless transmitter or the like. Similarly, any suitable connector 26 may be used for coupling the processor 24 with the data display device 25. In a preferred embodiment, the sensor device 21 may be coupled to the processor 24 through an anchor box 27 which houses signal conditioning or other electronic circuitry such as a wireless link. The processor also may be coupled to the existing nurse call system (not shown) of a hospital by any suitable connection. In a preferred embodiment, the processor 24 and display device 25 may be integrated into a single bedside unit.

A piezoelectric sensor generally acts as a strain gauge to measure changes in stress in the sensor. Detected stress changes may then be converted to electronic data useful for patient monitoring. A plurality of such sensors may be included in an array. The sensor array is placed under a patient, and, upon the application of a varying force due to movement of the patient's body, the piezoelectric sensors produce a small electrical voltage indicative of the varying applied force. When in use, each sensor element in the array may independently measure forces from the patient's body caused by the cardiac cycle, the respiratory cycle, and other physical movements and provide a representative voltage signal. Analysis is performed on these signals using digital processing techniques to separate the signals of interest from other physiological signals and noise. These types of sensors are advantageous when used in an array, because they can sense the signals of interest from the patient as long as the patient's body has some contact with the sensor array area. Sensing is not dependent upon specific placement of sensors in active areas to sense particular body functions.

Preferably, each piezoelectric sensor in the array is a thin film made of polyvinylidene fluoride (PVDF) polymer that is polarized during its original manufacture by a very strong electric field. After polarization, the molecular structures stay in alignment so that, when force is applied to the structure, a voltage difference between the top surface and the bottom surface is created. Silver ink or metal foils typically are applied to the top and bottom surfaces of the sensor element to allow detection of this voltage.

For a full description of the pressure sensing capabilities of piezoelectric films, their use for sensing patient parameters, and methods of processing the signals from these films to generate cardiac, respiratory or other signals of a patient, reference may be had to a co-pending application commonly assigned to the assignee of the present invention, Hoana Medical, Inc., namely, U.S. patent application Ser. No. 10/301,524 entitled "Devices and Methods for Passive Patient Monitoring," filed Nov. 20, 2002, (now published as U.S. Patent Publication No. 20040111045 on Jun. 10, 2004) the full disclosure of which is hereby incorporated by reference.

As previously noted, the sensor array 21 is designed to be attached to the patient's bed, under the bottom sheet, and not in direct contact with the patient's skin. The array is electronically connected or coupled to the bedside processor unit 24, which in turn, is coupled to a display and to an existing hospital nurse call system (not shown). Within the bedside unit 24 is a signal processor and an alarm processor that together measure the data from the sensor array and evaluate whether a clinically-significant event is occurring. The bedside unit may be a wall-mounted unit with a data display 25 that is activated when an alarm condition is enabled or on command by a nurse. The processor unit 24 may have a number of dedicated and softkey buttons and controls for entering information, setting up specific items and interacting with the system. The nurse call feature includes hardware, software and cabling to connect to a nurse call system already installed in the hospital or care facility. The signal processor 24 includes hardware and software that accepts, buffers and converts the sensor array 21 signal from analog to digital format for subsequent processing. The alarm processor uses logic functions to monitor the patient's parameter trends and determine when a negative condition is occurring. It then actuates the alarm circuitry for local and/or remote alarm.

In one embodiment, the processor activates an alarm if the comparison of the digital signals suggests that the patient is not moving on the surface, the patient is not in contact with the surface, or the patient is moving excessively on the surface. In another embodiment, the processor activates an alarm if a respiratory rate of the patient falls below a minimum respiratory rate or rises above a maximum respiratory rate. In yet another embodiment, the processor activates an alarm if a heart rate of the patient falls below a minimum heart rate or rises above a maximum heart rate. In other embodiments, an alarm may be activated if any combination of the above occurs. Some embodiments sound an alarm if a negative trend occurs, such as a negative heart rate trend, respiratory rate trend, patient movement or other trend or combination of trends. In some embodiments, the processor further provides the patient data in the form of a patient respiratory rate, heart rate or both. Preferably, the alarm is activated locally and over the existing nurse call system within the hospital.

Figure 2:
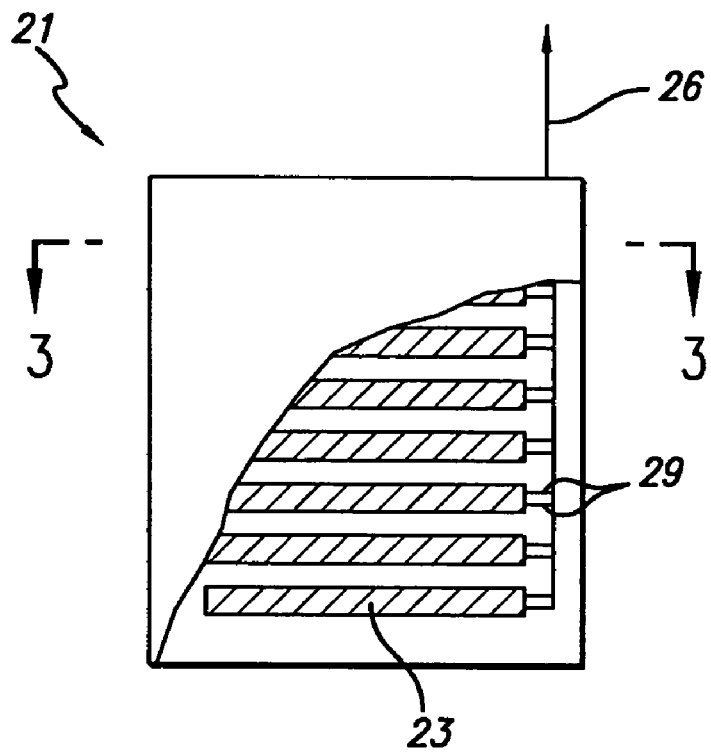
FIG. 2 is a partial cutaway plan view of an array of sensors forming a pad suitable for use as part of a passive patient monitoring system in accordance with the present invention.
Figure 3:
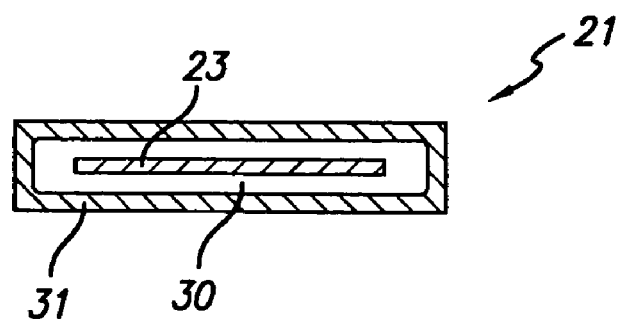
FIG. 3 is a cross-sectional view taken substantially through line 3-3 of FIG. 2.
Figure 2A:
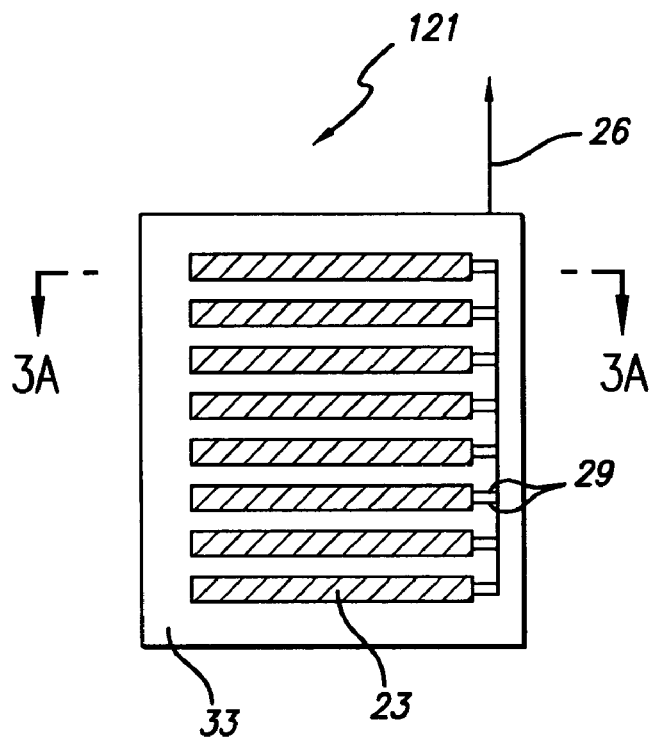
FIG. 2A is a top view of an alternative embodiment of the sensor array shown in FIG. 2.
Figure 3A:
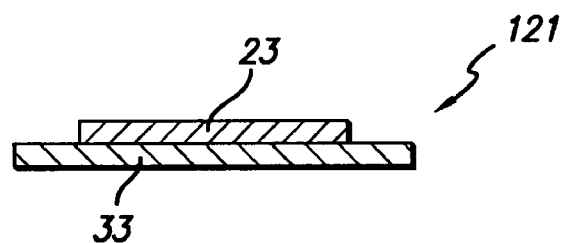
FIG. 3A is a cross-sectional view taken substantially through line 3A-3A of FIG. 2A.

The plurality of piezoelectric films 23 in the sensor array 21 may assume any configuration or number, individually, and in relation to each other. For example, as exemplified in FIGS. 2-3, the sensor array 21 may include an array of at least eight piezoelectric sensor elements 23 arranged adjacent and parallel to each other in a vertical column. In this example, each sensor element is paper thin, or thinner, and forms a thin flat elongate rectangular strip approximately twenty four inches by three quarters of an inch. Each sensor element also includes a set of terminals 29 which are connected to a suitable connector 26 that communicates the sensor signal to the bedside unit 24 (FIG. 1). In one embodiment, each sensor element 23 and the entire sensor array 21 may be protected, on both top and bottom surfaces, by soft foam padding 30 such as neoprene for patient comfort. (FIG. 3) Surrounding the soft padding and enclosing the entire array, is an external moisture barrier 31 which provides an impervious outer surface protecting the sensors in the array from fluids or other contaminants and also providing an additional electrical isolation. The overall thickness of the sensor pad array is typically between 1 mm-7 mm, and preferably less than 5 mm thick, and forms a flexible, thin rectangular pad of approximately thirty two inches by twenty four inches, large enough to span almost the entire width of the bed, and to extend across the patient's torso from shoulders to buttocks. If desired, additional sensors or sensor arrays can be positioned in the bed under the patient's legs for monitoring bed elopement and leg movement.

Alternatively, as exemplified in FIG. 2A-3A, each sensor element 23 in the array may be connected directly to the surface of a carrier sheet 33 by suitable adhesive or bonding material, to provide a significantly thinner sensor device that will less readily be detected by the patient. For example, a sensor array mounted on the surface of a urethane carrier sheet by adhesive may be less than 1 mm, and preferably less than 200 μm, thick.

It will be appreciated that the sensor pad or carrier arrangements described may be easily handled and cleaned, and are suitable for placing in the patient's bed under the sheets to form part of the patient's sleep surface. Because the sensors are not directly in contact with the skin of the patient, they can be made more compliant than an array that depends on direct skin contact or specific body position or orientation. This allows the array to be more easily attended to or integrated more closely with the mattress surface or interior, as desired, without necessarily being built into the bed or mattress in a permanent manner. Instead, by using the locations and methods of attachment described in greater detail below, the sensor array can be easily and inexpensively retro-fit to an existing bed without replacing the entire bed or mattress.

It will be appreciated that a typical hospital bed comprises a bed frame and a mattress assembly. A medical mattress assembly typically has a foam core surrounded by a waterproof coverlet, typically made of a low friction urethane or butyl coated fabric and supplied by the mattress manufacturer as a part of the mattress assembly. The coverlet normally has a bottom portion below, and a top portion above, the mattress core. In most cases, the coverlet is replaceable and is closed around the core with a zipper or similar arrangement on at least one side of the mattress core. The coverlet, which can act as a vapor permeable moisture barrier, is usually wiped down with germicides by housekeeping personnel between patients. Washable bed sheets, either fitted sheets or flat sheets, are typically placed over the mattress coverlet. In some cases, an underlayer, typically made of a stretchable low weight mesh or gauze, or a thin polyurethane film, is supplied by the manufacturer to act as a vapor barrier between the coverlet and the core, preventing moisture vapor from entering the foam core and providing a smooth, slippery interface between the coverlet and the foam core.

In accordance with the present invention, the thin sensor pad or carrier sheet assembly used to passively monitor the patient's physiological conditions and movement is securely affixed to the coverlet in the patient's mattress assembly, to an additional coverlet placed securely over the mattress assembly, or to an additional or existing layer disposed between the mattress core and coverlet, where it lies smooth and flat when in use, under the sheets or other bedding, substantially hidden from the patient and hospital staff. This flexible pad or carrier sheet assembly is comfortable for a patient lying on top of the bed, and may be conveniently deployed on a variety of different types of medical mattress without undue interference with the desired mattress properties.

Figure 4:
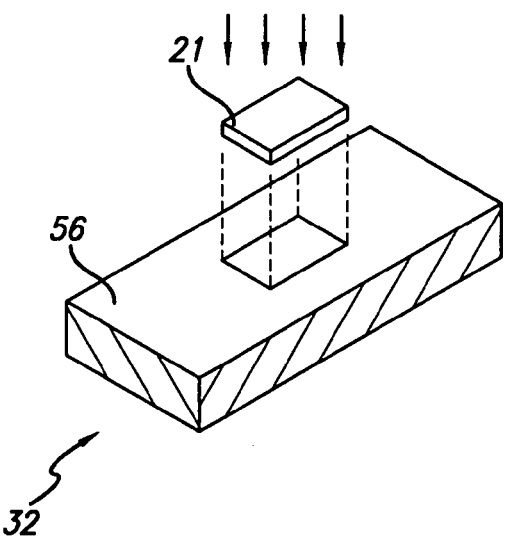
FIG. 4 is an exploded perspective view of a mattress assembly, showing the sensor pad of FIG. 2 or 2A, reduced in size, being attached directly to the outer surface of the mattress.

In one embodiment, exemplified in FIG. 4, a sensor array 21 provided in the form of a separate freestanding pad or carrier sheet as previously described is arranged to be placed directly against the top or bottom surface of the mattress assembly 32, on the outside of the coverlet 56. Such pad or carrier sheet may be protected by a covering envelope or other protective layer (not shown), or may be protected by the bed sheets alone. The pad or carrier may be permanently or removably connected to the mattress coverlet surface in a desired location in a variety of different ways.

For example, a simple and inexpensive method of attachment is by bonding, wherein an adhesive layer or a double-sided adhesive film may be applied between the underside of the sensor pad or carrier sheet 21 and the outside of the coverlet 56. Adhesive has the advantage of effectively securing the pad or carrier sheet 24 to the coverlet 56, while making the pad or carrier sheet 21 selectively removable from the coverlet 56 for replacement or repair. A removable release liner can be applied to the exposed tacky side of the adhesive backing for ease of handling, storage and transport of a sensor pad or carrier sheet before it is attached to the mattress.

Alternatively, permanent bonding agents can also be used such as glues, epoxies, chemical bonders, and the like, in lieu of the adhesive backing. Suitable permanent bonding methods also include radio frequency welding, ultrasonic welding, and heat sealing. Mechanical bonds are also possible such as stitching or sewing of the pad or carrier sheet to the coverlet for a permanent attachment, or using hook and loop (Velcro™) fasteners, or providing a high friction interface between the pad or carrier sheet and the coverlet, for a releasable attachment.

Figure 5:
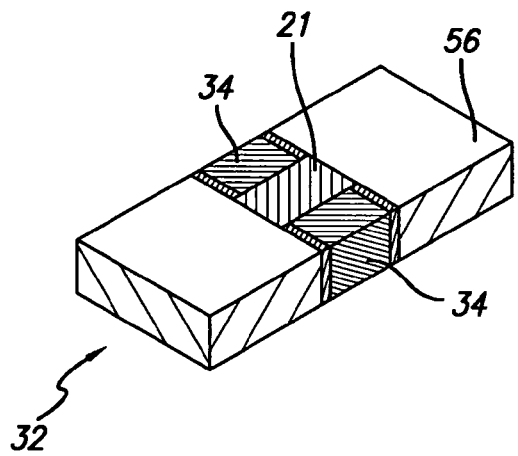
FIG. 5 is a perspective view of a mattress assembly, showing another method of attaching the sensor pad of FIG. 4 to the surface of the mattress, using wide straps.
Figure 6:
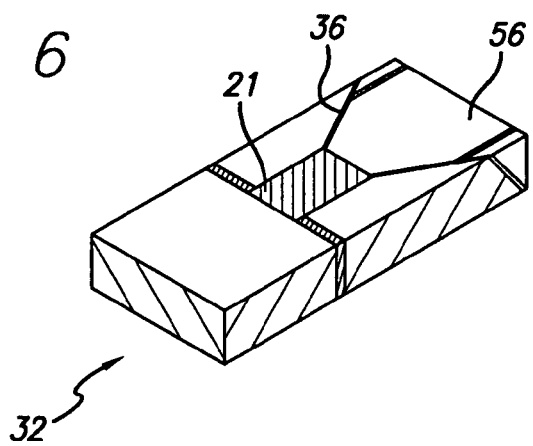
FIG. 6 is a perspective view of a mattress assembly, showing yet another method of attaching the sensor pad of FIG. 4 to the surface of the mattress, using narrow straps.
Figure 7:
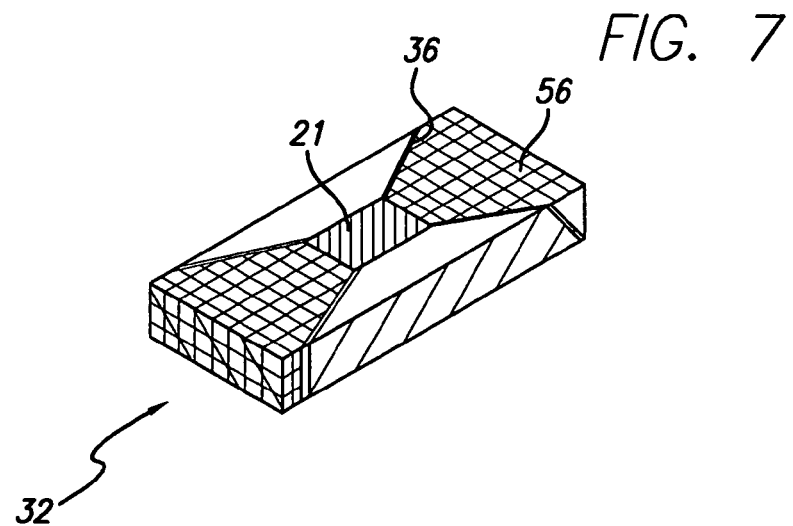
FIG. 7 is a perspective view of a mattress assembly, showing still another method of attaching the sensor pad of FIG. 4 to the surface of the mattress, using webs.

In an alternative method, shown in FIGS. 5-7, the sensor pad or carrier sheet 21 may be attached to the mattress assembly 32 by using straps. As exemplified in FIG. 5, wide straps 34 joined to the sides of the pad or carrier sheet 21 may be positioned to run laterally around, or partially around, the mattress assembly 32 so as to hold the pad or carrier sheet 21 against a top or bottom surface of the mattress assembly 32. The straps can be in the form of a continuous band that extends around the mattress assembly, or they can be formed as segments that join together with buckles, hook and loop (Velcro™) fasteners, or some other kind of attachment. Straps that run only partially around the mattress fit under the mattress and are held in place by the weight of the mattress and the patient. In another aspect, exemplified in FIG. 6, narrow straps 36 connected to the corners of the pad or carrier sheet 21 may be oriented in a multitude of ways such as laterally, lengthwise diagonal to corners of the mattress, or a combination of the two, effectively holding the pad or carrier sheet against the mattress assembly 32. Alternatively, as shown in FIG. 7, webs of elastic or stretchable material can be used that extend from opposite sides of the pad or carrier sheet to provide multi-directional support, such as webs that capture two corners and the shared surface such as the top two corners of the mattress assembly. Alternatively, a system of large and wide straps can be used. Such straps may go entirely around the mattress assembly or just to the sides or underside. Sections of the straps may incorporate one of the securing methods listed above, such as temporary or permanent bonding. Straps or webs that secure the pad or carrier sheet to the corners of the mattress assembly, such as those shown in FIGS. 6-7, provide enhanced positional stability.

Figure 8:
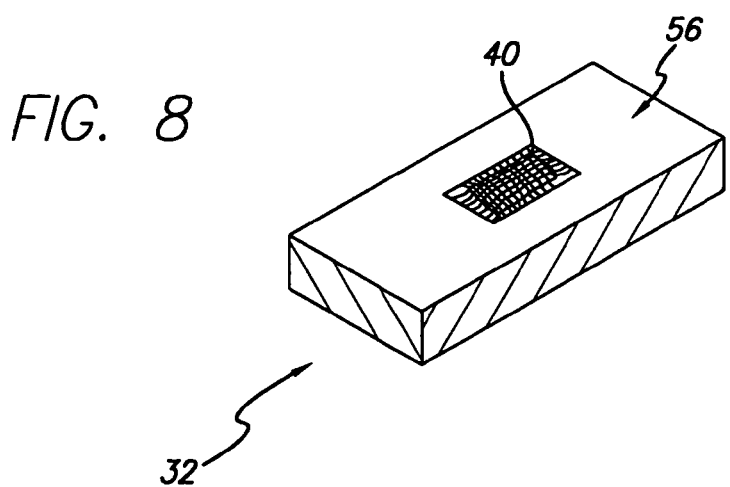
FIG. 8 is a perspective view of a mattress assembly, showing still another method of attaching the sensor pad of FIG. 4 to the surface of the mattress, using a membrane.
Figure 9:
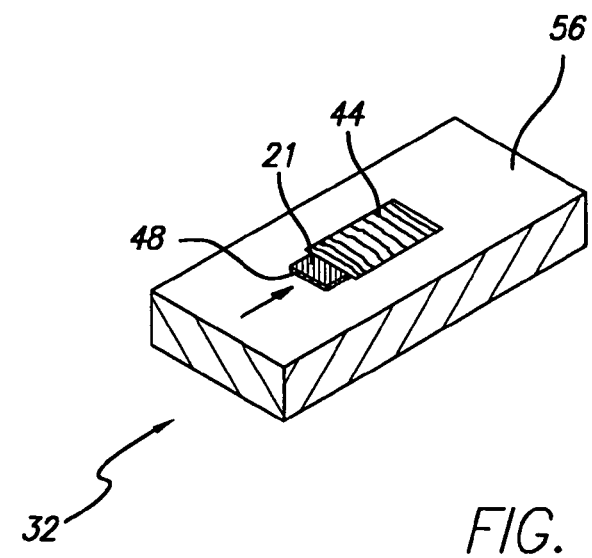
FIG. 9 is a perspective view of a mattress assembly, showing yet another method of attaching the sensor pad of FIG. 4 to the surface of the mattress, using an envelope or pocket.

In yet another aspect, the sensor pad or carrier sheet 21 may be placed within or under a protective layer attached to the mattress assembly to hold the pad or carrier sheet against the coverlet surface of the mattress assembly 32. For example, as shown in FIG. 8, a protective layer 40 may be a single layer of material that covers the exposed side of the pad or carrier sheet 21 (not shown in FIG. 8), sandwiching the pad or carrier sheet between the layer 40 and the mattress assembly coverlet. In another aspect, as shown in FIG. 9, the pad or carrier sheet 21 may be held against the mattress assembly 32 by a sheet of fabric forming a pocket or envelope 44 of material that encloses and protects the pad or carrier sheet and allows the pad or carrier sheet to be inserted and removed through an opening 48 along an edge of the pocket or envelope. By closing the opening 48 with an adhesive layer or hook and loop (Velcro™) fastener, the pad or carrier sheet can be made selectively removable from the pocket or envelope. The protective layer 40, or the pocket or envelope 44, may be formed of any suitable material or combination of materials preferably having some degree of water resistance, such as Tyvek™ (a non-woven high density polyethylene material) to protect the sensor pad or carrier sheet from urine, water, blood, or any other fluid that may be spilled on the patient's bed, and may be placed either on the top side or bottom side of the mattress assembly. The protective layer can be secured to the mattress coverlet 56 using any of the methods listed above, such as temporary or permanent bonding. In one embodiment, the protective layer may be disposable and used for only one patient, for only one day, or the like. In an alternative embodiment, the protective layer 40 or pocket or envelope 44 could be used to hold a sensor pad or carrier sheet against the surface of the sheets or other conventional bedding, instead of the mattress coverlet.

When a water resistant protective layer is used to hold a pad 21 against the mattress assembly 32, the external moisture barrier that forms a part of the sensor pad may be replaced with a stretchable mesh or gauze material, that fits more loosely around the sensor elements, potentially improving sensor signal characteristics and patient comfort. The water resistant protective layer can be made disposable and does not need to be cleaned.

In a further alternative embodiment, exemplified in FIGS. 10-13, the sensor array in the form of the pad or carrier sheet previously described, may be integrated into the coverlet. This may be achieved by replacing the conventional coverlet with a new coverlet containing the sensor array as an integral part thereof. Alternatively, the existing mattress assembly with its conventional coverlet may be surrounded with an additional new mattress cover or coverlet containing the sensor array. Both alternatives may utilize a number of alternative ways, alone or in combination, for removably attaching the cover or coverlet to the mattress. These may include a zipper, hook and loop fasteners (for example Velcro™), or straps to attach the new or replacement cover or coverlet to the mattress, or by gathering and holding the cover or coverlet around the base of the mattress using, for example, elastic, string, or clips.

The additional replacement cover or coverlet may be formed of more than one material, such as a patient contact material on one side and an underside material on the opposite side. The sensor array may be disposed between the two layers of material, which are then sealed together to hold the array in place. At least one opening may be present in the cover or coverlet to allow insertion of the mattress core inside. The location, shape and size of this opening is variable as are the methods of closing it.

Figure 10:
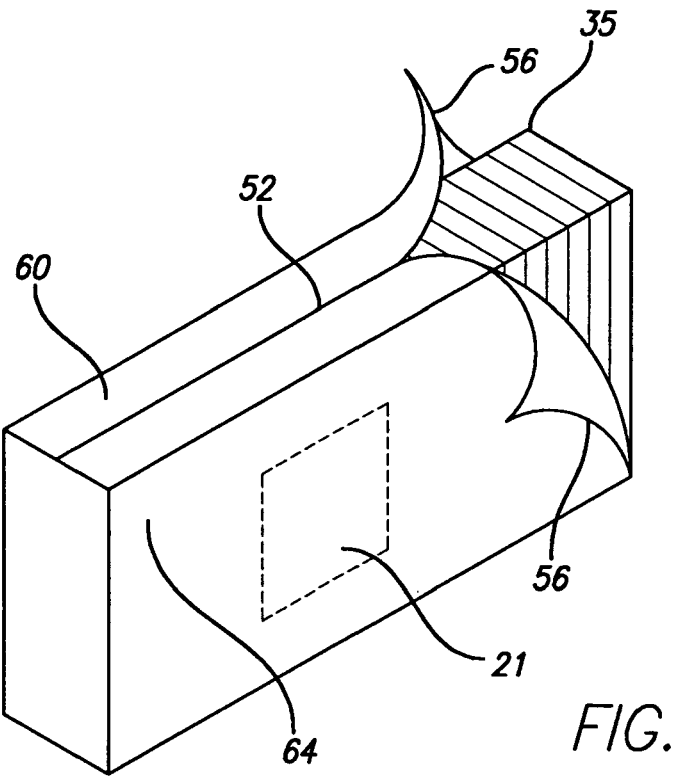
FIG. 10 is a perspective view of a mattress assembly, showing a method of enclosing the mattress core in a coverlet which has the sensor pad of FIG. 4 embedded therein.
Figure 11:
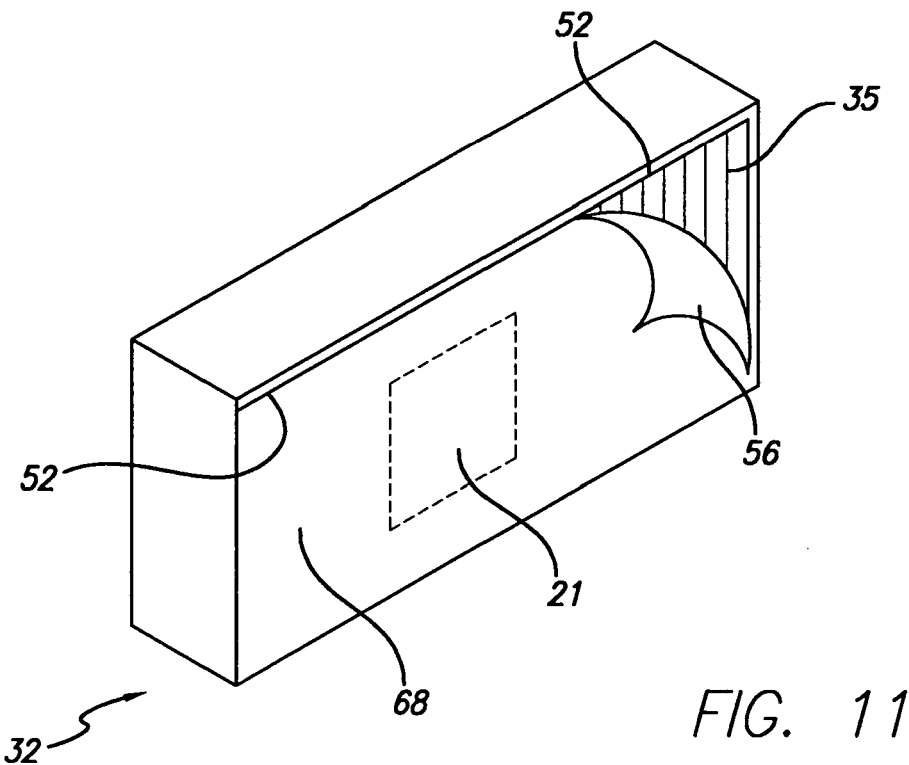
FIG. 11 is a perspective view of a mattress assembly, showing an alternative method of enclosing the mattress core in a coverlet which has the sensor pad of FIG. 4 embedded therein.

In one embodiment, as shown in FIG. 10, a zipper 52 may be used to close a seam in the cover or coverlet 56. The cover or coverlet 56 may consist of two halves 60, 64 that are zippered 52 together along all four sides of the mattress at the height midline or are zippered together along only one, two or three sides. Alternatively, as shown in FIG. 11, zippers 52 can be placed entirely on the bottom surface 68 of the cover or coverlet 56 rather than on a side and used to close a seam around the perimeter of the bottom surface 68. Hook and loop (Velcro™) fasteners, and adhesive tape are also suitable for closing up overlapping seams of an opening in the cover or coverlet.

Figure 12:
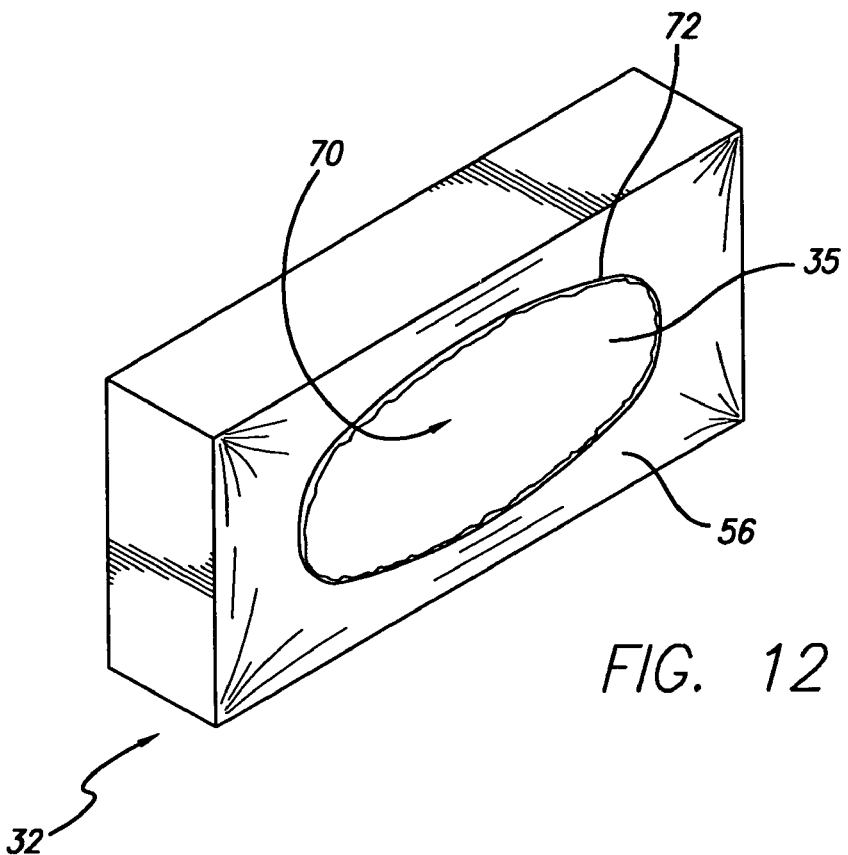
FIG. 12 is a perspective view of a mattress assembly, showing a further alternative method of enclosing the mattress core in a coverlet which has the sensor pad of FIG. 4 embedded therein.

In another aspect, exemplified in FIG. 12, a large opening 70 is provided at the bottom of the coverlet 56 for receiving the mattress core 35. The perimeter of fabric surrounding the opening then may be gathered together and tied, to create tension in the coverlet and prevent slippage. In one alternative, an elastic band 72 may be threaded either fully or partially through a hem at the edge of the cover or coverlet, to pull the cover or coverlet automatically into a tight arrangement. In another alternative, a string may be threaded through the hem, in which case the string is manually pulled together via a drawstring to synch and reduce the size of the opening.

Figure 13:
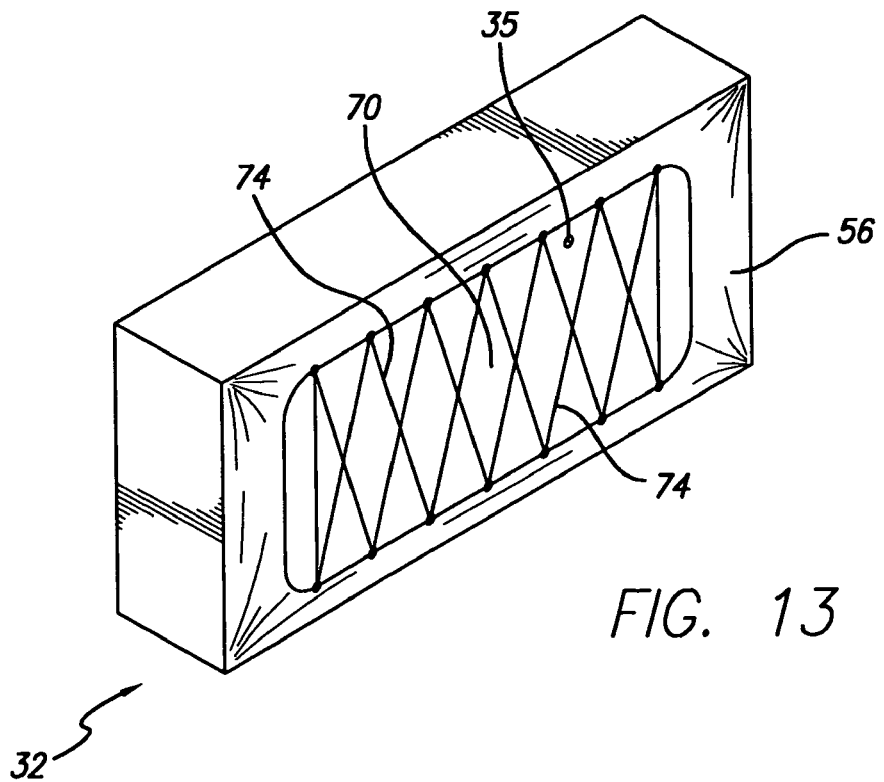
FIG. 13 is a perspective view of a mattress assembly, showing yet a further alternative method of enclosing the mattress core in a coverlet which has the sensor pad of FIG. 4 embedded therein.

In yet a further alternative, exemplified in FIG. 13, straps may be used to tension the cover or coverlet 56 around the mattress core 35. On the underside of the cover or coverlet, a plurality of straps 74 or ties may be arranged to extend across an opening 70 in the cover or coverlet in a zig-zag or criss-cross fashion to permit the straps 74, and hence the cover or coverlet, to be tensioned so as to hold the cover or coverlet securely in place. Preferably, the straps engage and pass through a series of eyelets disposed along the edge of the cover or coverlet.

In yet a further alternative, magnets (not shown) may be attached to the inside of the cover or coverlet on the underside of the mattress and adhered to the bed frame to achieve a suitable tension in the cover or coverlet to secure it in place.

Figure 18:
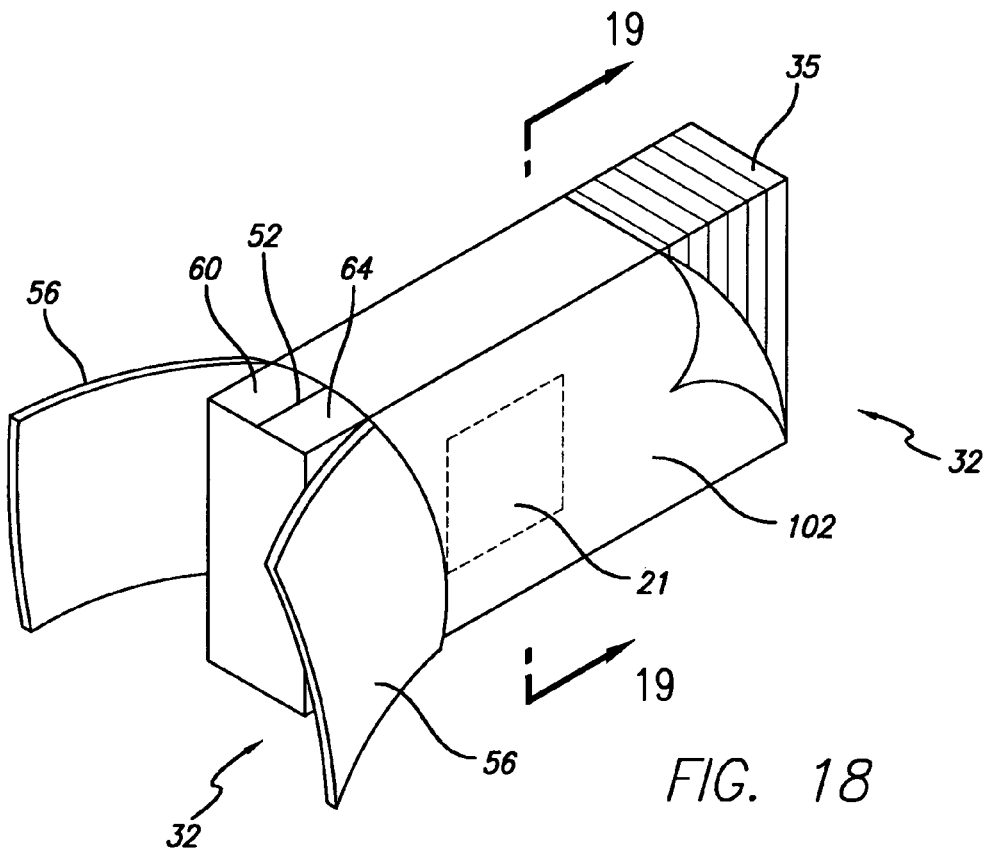
FIG. 18 is a perspective view of a mattress assembly, showing a mattress core encased in a coverlet with an underlayer placed between the coverlet and the mattress core and the sensor array of FIG. 4 embedded in the underlayer, with portions of the mattress assembly separated to show the construction thereof.
Figure 19:
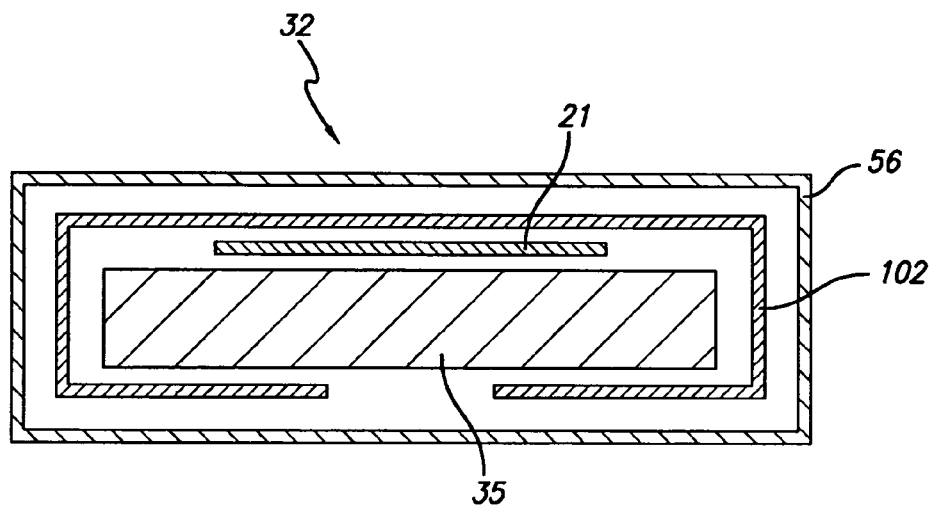
FIG. 19 is a sectional view through the mattress assembly of FIG. 18, substantially along line 19-19, when the mattress core is fully enclosed by the coverlet.

In a presently preferred aspect of the invention, exemplified in FIGS. 18 and 19, the sensor array 21 may be attached to or embedded in an underlayer 102 disposed between the coverlet 56 and the mattress core 35. The underlayer is preferably a thin urethane film which is placed around and secured to the core 35 like a fitted sheet and enclosed by the coverlet (FIG. 19). The sensor pad may be attached to the inner or outer surface of the underlayer above the core 35 using any of the methods described as suitable for attaching the sensor pad or carrier sheet to the coverlet 56. This arrangement may be achieved by replacing the conventional underlayer with a new underlayer containing the sensor array as an integral part thereof. Alternatively, the sensor array can be attached to the existing underlayer or to an additional underlayer placed over the existing underlayer. Attaching the sensor array to the underlayer can help protect the array from moisture and provides extra patient comfort due to the additional layers of material between the patient and the sensor array.

All of the approaches described for attaching the sensor array to an existing coverlet (FIGS. 4-9), for integrating it into a replacement or additional coverlet (FIGS. 10-13) or attaching or integrating it into an existing, additional, or replaced underlayer (FIGS. 18-19) have the advantage of integrating the sensor directly into the mattress assembly, while allowing the sensor to be effectively changed or replaced without replacing the entire mattress assembly.

In a further embodiment, the sensor array of the present invention may also be integrated within the mattress core itself, either by replacing the mattress core, by positioning the array within the existing mattress core, or by positioning the array between the mattress core and the top or bottom portions of the mattress coverlet.

Figure 14:
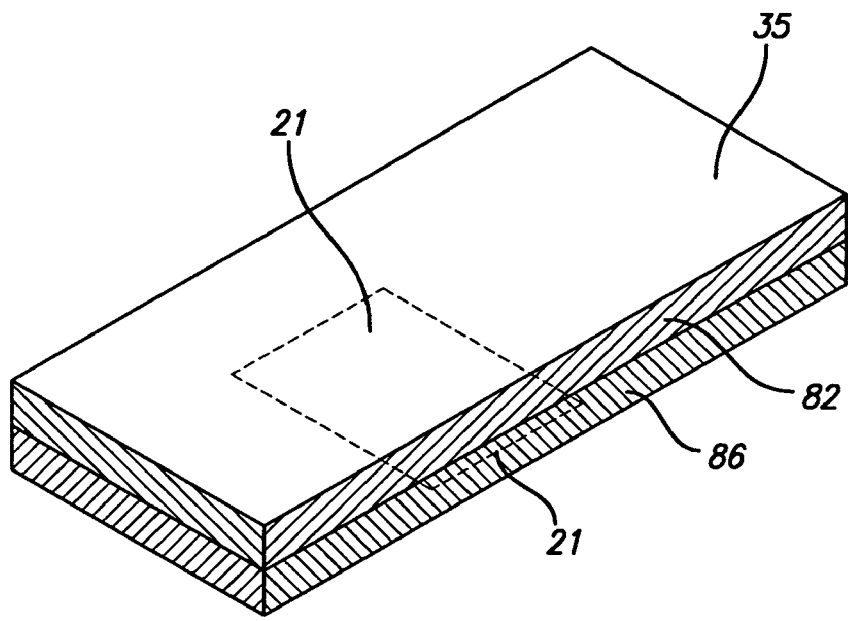
FIG. 14 is a perspective view of a mattress assembly, showing the sensor pad of FIG. 4 embedded between layers of the mattress core.
Figure 15:
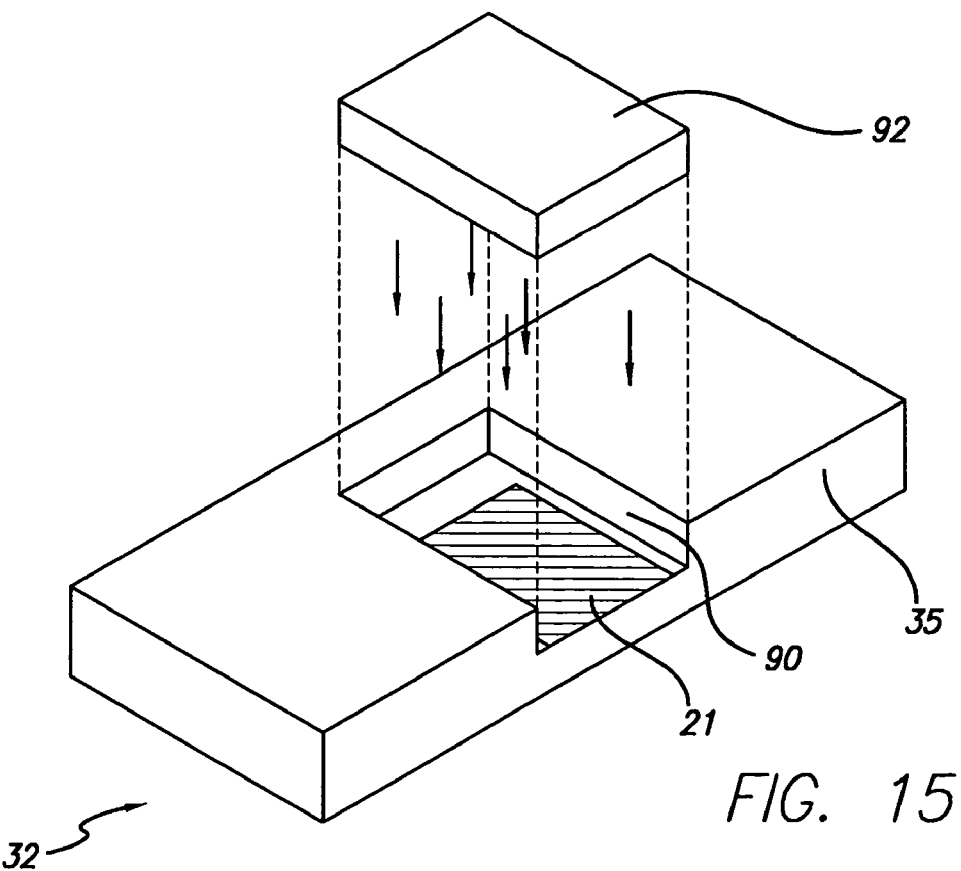
FIG. 15 is an exploded perspective view of a mattress assembly, showing the sensor pad of FIG. 4 placed within a cavity in the mattress core formed by removing a block of mattress core material.

For example, as exemplified in FIGS. 14-15, the array 21 may be placed within an existing mattress core 32, either between layers 82, 86 of foam or other material that make up the core (FIG. 14) or by creating a pocket 90 or opening in the core (FIG. 15) and inserting the sensor pad or carrier sheet 21. Preferably, the pocket is formed by removing a rectangular block 92 of material from a surface of the foam core. The pad or carrier sheet can be secured within the pocket by the use of bonding anchors or straps, in the same way that a freestanding pad or carrier sheet can be attached to the outside surface of the coverlet. Preferably, the block 92 of material removed from the core is replaced and secured by any suitable means once the pad or carrier sheet is placed in the opening. Alternatively, the entire mattress core can be manufactured with the sensor elements inside so that it is one integrated unit. This core could then be inserted into a conventional mattress coverlet to replace the existing mattress core.

In yet another alternative (not shown), the sensor pad or carrier sheet 21 can be placed between the mattress coverlet 56 and the mattress core 35 either on the top side of the mattress core or on the underside. The pad or carrier sheet 21 can be secured to the adjacent core 32 or the adjacent coverlet 56. Either way, most all of the previously disclosed attachment methods are appropriate.

Figure 16:
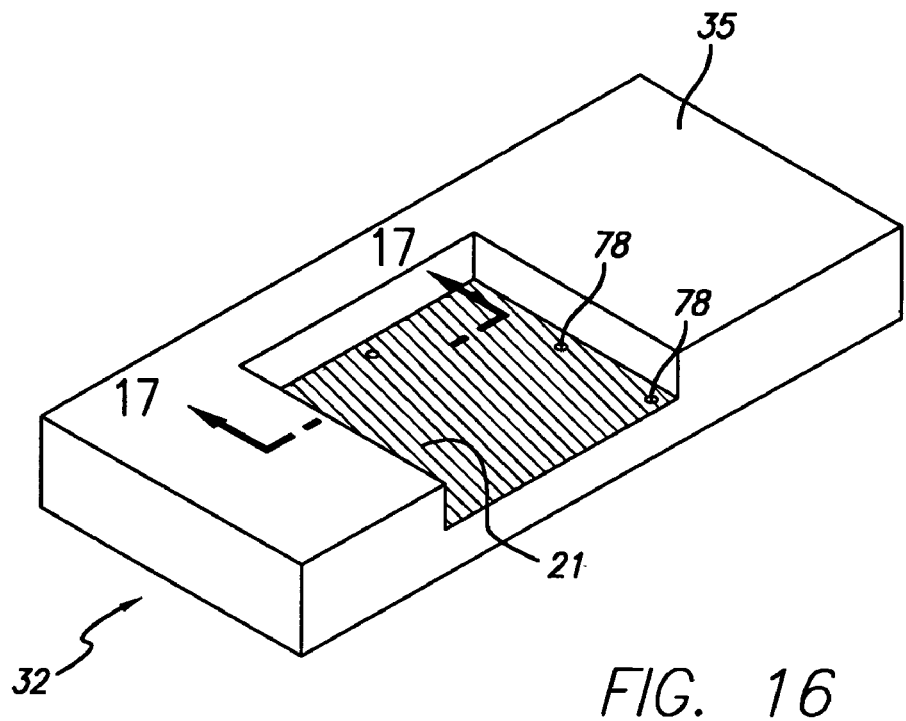
FIG. 16 is a perspective view of a mattress assembly, showing the sensor pad of FIG. 4 attached to the surface of the mattress core by anchors.
Figure 17:
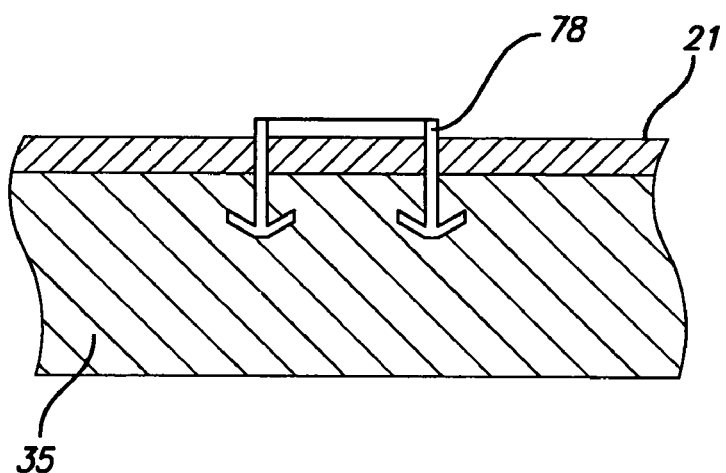
FIG. 17 is a fragmentary sectional view, taken substantially along line 17-17 of FIG. 16.

If the pad or carrier sheet 21 is relatively small, bonding and straps are suitable methods of attachment. Alternatively, the sensor pad or carrier sheet 21 may be mechanically attached to the mattress core 35. FIGS. 16-17 exemplify the manner in which small barbed anchors 78 may be placed through a sensor pad or carrier sheet 21 and set into the mattress core to secure the sensor pad or carrier sheet 21 in place. These anchors 78 may be removably or permanently set. Multiple locations for anchors 78 will likely be needed, such as at each corner of the pad or carrier sheet 21 or around the perimeter of the pad or carrier sheet. It will be appreciated that anchors 78 may be set on any surface of the mattress core.

A large pad or carrier sheet resembling the shape of a cover may be wrapped around the mattress core and be secured by the methods described above for attaching a new cover or replacement coverlet to a mattress core. These include seam closure, elastic or string gathers, straps, or magnets.

It will be appreciated that the sensor array used in any of the foregoing embodiments also can be made of free-standing sensor elements that are assembled and attached discretely and separately to the corresponding portions of the mattress assembly, rather than being mounted to a pre-formed sensor pad or carrier sheet. However, use of the pad or carrier sheet can help insure proper relative positioning of the sensor elements, provide additional structural support for the sensor films, and facilitate ease of removal or attachment of the sensor array to the mattress assembly.

Figure 20:
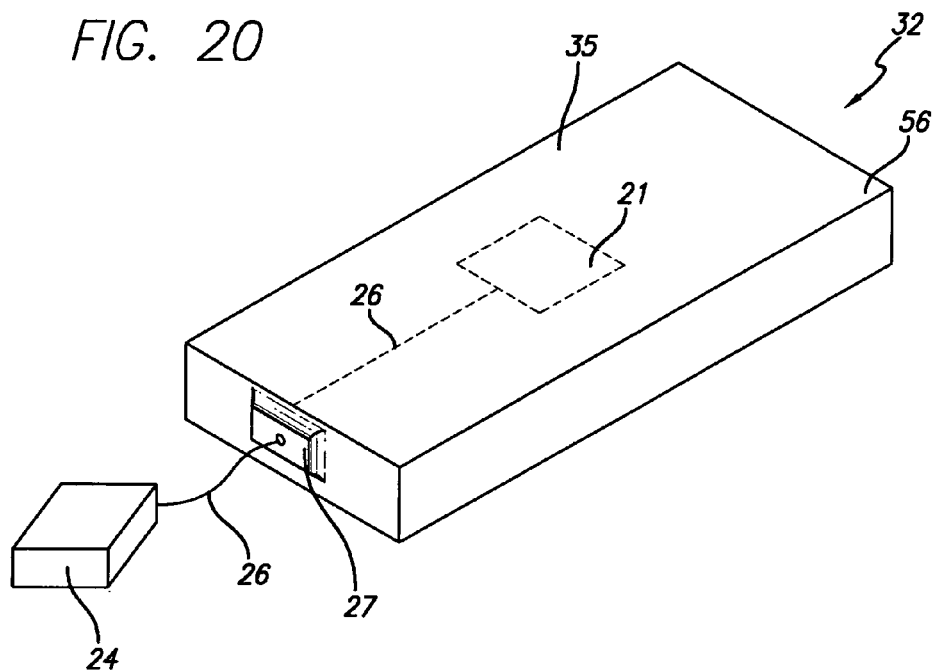
FIG. 20 is a perspective view of a mattress assembly, showing the relative positions of a sensor array and an anchor box attached to a coverlet.
Figure 21:
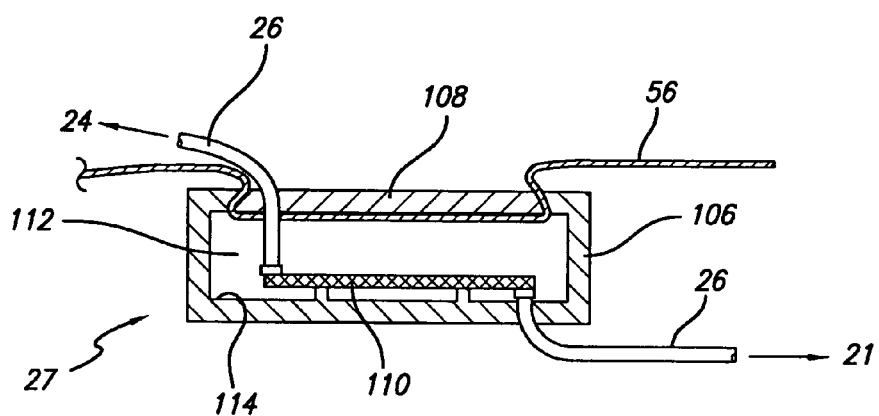
FIG. 21 is a sectional view of an anchor box attached to a coverlet.

In yet another aspect of the invention, an apparatus and method is provided for connecting the processor 24 to the sensor pad or carrier sheet 21. It may be found that a problem sometimes arises with regard to the connector cable 26 extending between processor 24 and the sensor 21 in that accidental force applied to the cable 26 may damage the connection to the sensors or dislodge the sensor array 21 from its desired location. In the present invention, the problem may be solved by firmly attaching an anchor box 27 to the coverlet 56, as shown in FIG. 20. The connector cable 26 is arranged to extend from the processor 24 to the anchor box 27 so that accidental forces applied to the cable 26 are transmitted into the coverlet 56 via the anchor box, and are not transmitted to the sensor array 21 itself. As exemplified in FIG. 21, the anchor box 27 may comprise a housing 106 and a lid 108 which together define an enclosed box with an internal space 112. A printed circuit board 110 is mounted within the internal space, and the connector cable 26 is arranged to extend from the processor 24 (not shown in FIG. 21), through an aperture provided in the lid 108 of the anchor box to the printed circuit board 110. The connector cable 26 is further arranged to extend from the printed circuit board to the sensor array 21 (not shown in FIG. 21), passing through another aperture, preferably in the bottom surface 114 of the housing. In a preferred embodiment, the lid 108 may be configured in relation to the housing 106 so that, if the lid is placed outside the coverlet 56 and the housing is placed inside the coverlet in juxtaposition with the lid 108, the lid 108 may engage the housing 106 with a snap fit to achieve a sealed connection while trapping the fabric of the coverlet 56 between the lid 108 and the housing 106 so that the anchor box 27 is held fixedly in place on the surface of the coverlet, with the beneficial result as described above.

From the foregoing, it will be appreciated that the present invention allows a passive sensor or sensor array to be integrated into a patient's mattress in a variety of different ways to support continuous passive monitoring in a hospital setting. The thin, flexible sensors are comfortable for the patient to lie on and are hidden from both the patient and hospital staff when in use. The sensors maintain the desirable properties of the medical mattress yet are rugged enough to withstand being crumpled or creased by the movement of the patient.

While the specification describes particular embodiments of the present invention, it will also be apparent to those of ordinary skill that various modifications can be made without departing from the spirit and scope of the invention.

We claim:

1. A system to support continuous passive monitoring of a patient, comprising:
    a passive sensor for monitoring the patient;
    a mattress core; and
    a coverlet configured to surround the mattress core;
    wherein the sensor is attached to the coverlet between a protective layer and a surface of the coverlet, the protective layer being attached to the coverlet; and
    wherein the protective layer forms an envelope that encloses the sensor and allows the sensor to be selectively inserted and removed.

2. The system of claim 1, wherein the coverlet defines an opening for inserting the mattress, the coverlet including a zipper configured to seal the opening, whereby the coverlet surrounds the mattress when the opening is sealed.

3. The system of claim 1, wherein the coverlet includes two halves and a zipper configured to joint the two halves together.

4. A system to support continuous passive monitoring of a patient, comprising:
    a passive sensor for monitoring the patient;
    a mattress core; and
    a coverlet configured to surround the mattress core;
    wherein the sensor is attached to the coverlet by at least two straps connected to the sensor, the straps being configured to extend entirely around the mattress core to hold the sensor in position, wherein some of the at least two straps are formed as segments joined together with a connector selected from the group of buckles and hook and loop fasteners.

5. The system of claim 4, wherein the coverlet has a lengthwise dimension and a lateral dimension, and at least one strap is a continuous band that extends laterally entirely around the coverlet.

6. The system of claim 4, wherein the coverlet has a plurality of corners, and at least two straps extend from the sensor and engage adjacent corners of the coverlet.

7. A system for securing a passive sensor to a mattress assembly, the mattress assembly including a core and a coverlet surrounding the core, said system comprising:
    a housing having an opening;
    a removable lid configured to seal the opening, the lid and housing together defining a space when the lid seals the opening;
    a circuit board positioned within the space;
    a first cable extending from the circuit board for connection to a processor;
    a second cable extending from the circuit board for connection to the sensor;
    wherein the lid and housing are configured to capture a portion of the coverlet when the lid seals the opening, thereby holding the housing in a fixed position relative to the coverlet.

8. The system of claim 7, wherein the coverlet defines an opening for inserting the core, the coverlet including a zipper configured to seal the opening, whereby the coverlet surrounds the core when the opening is sealed.

9. The system of claim 8, wherein the zipper is positioned in relation to the coverlet to extend substantially along a height midline of the mattress when the coverlet surrounds the core.

10. The system of claim 8, wherein the zipper is positioned in relation to the coverlet to extend substantially along an edge of the core when the coverlet surrounds the core.

11. The system of claim 7, further comprising:
    an underlayer positioned between the mattress core and the coverlet;
    wherein the sensor is attached to the underlayer.

12. The system of claim 11, wherein the underlayer includes two layers of material sealed together to hold the sensor array therebetween.

13. The system of claim 11, wherein the sensor is attached to a surface of the underlayer using adhesive.

14. The system of claim 11, wherein the sensor is attached to a surface of the underlayer using a bonding method selected from the group consisting of radio frequency welding, ultrasonic welding, and heat sealing.

15. The system of claim 11, wherein the sensor is attached to a surface of the underlayer using an attachment method selected from the group consisting of sewing, hook and loop fasteners, and high friction.

16. The system of claim 7, wherein the sensor is embedded within the core.

17. The system of claim 16, wherein the core includes a first layer and a second layer, wherein each layer extends substantially over the length of the core, the sensor being positioned between the first layer and the second layer.

18. The system of claim 16, wherein a pocket is formed in a portion of the core, the sensor being positioned within the pocket and covered by a layer of core material which closes the pocket.

19. The system of claim 16, wherein the sensor is attached to a surface of the core by a permanent anchor.

20. The system of claim 16, wherein the sensor is attached to a surface of the core by a removable anchor.

21. The system of claim 7, wherein the housing and lid are configured to produce a snap fit connection to each other.

22. The system of claim 7, wherein the sensor is attached to a surface of the coverlet using adhesive.

23. The system of claim 7, wherein the sensor is attached to a surface of the coverlet using a bonding method selected from the group consisting of radio frequency welding, ultrasonic welding, and heat sealing.

24. The system of claim 7, wherein the sensor is attached to a surface of the coverlet using an attachment method selected from the group consisting of sewing, hook and loop fasteners, and high friction.

25. The system of claim 7, wherein the coverlet includes two layers of material sealed together to hold the sensor therebetween.

26. The system of claim 7, wherein the sensor is attached to the coverlet between a protective layer and a surface of the coverlet, the protective layer being attached to the coverlet.

27. The system of claim 7, wherein the passive sensor includes an array of pressure sensing elements.

28. The passive sensor system of claim 27, wherein the pressure sensing elements include piezoelectric sensors.

29. The passive sensor system of claim 27, wherein the pressure sensing elements each have two opposite surfaces, each surface being protected by a foam padding.

30. The passive sensor system of claim 27, wherein the passive sensor includes a carrier sheet to which the pressure sensing elements are attached, the adhesive layer being attached to the carrier sheet.

31. The system of claim 7, wherein the passive sensor includes a sensor array disposed upon a carrier sheet attached to the coverlet.

32. The system of claim 31, wherein the sensor array is attached to a surface of the carrier sheet using adhesive.

33. The system of claim 31, wherein the sensor array includes piezoelectric sensing elements and pressure switches.

34. The system of claim 31, wherein the carrier sheet is formed of a urethane material.

35. The system of claim 31, wherein the carrier sheet is attached to an inner surface of the coverlet, so that the carrier sheet is disposed between the coverlet and the mattress core when the coverlet surrounds the mattress core.

36. The system of claim 31 wherein the carrier sheet is attached to the coverlet by welding.

37. The system of claim 31, wherein sensors in the sensor array are formed of a polarized polymer film.

38. The system of claim 31, wherein the carrier sheet is detachably connected to the coverlet.

39. The system of claim 31, wherein the carrier sheet is detachably connected to the coverlet with a hook and loop fastener.

40. The system of claim 31, wherein the carrier sheet is placed against the top surface of the mattress assembly.

41. The system of claim 31, wherein the carrier sheet is placed against a bottom surface of the mattress assembly.

42. The system of claim 7, wherein the coverlet includes two halves and a zipper configured to join the two halves together around the mattress core.

43. The system of claim 7, wherein the lid and housing are configured to capture a portion of the coverlet along an end of the mattress.

44. A system for connection to a mattress to support continuous passive monitoring of a patient, comprising:
a passive sensor for monitoring the patient; and
a coverlet configured to substantially surround the mattress;
wherein the sensor is attached to the coverlet and the coverlet is configured to define an opening for inserting the mattress, and wherein a hem surrounds the opening, the hem containing an elastic band configured to reduce the size of the opening when the elastic band is allowed to contract.

45. The system of claim 44, wherein the coverlet includes two layers of material sealed together to hold the sensor therebetween.

46. The system of claim 44, wherein the sensor is attached to a surface of the coverlet using an adhesive layer.

47. The system of claim 44, wherein the sensor is attached to a surface of the coverlet using a double-sided adhesive film.

48. The system of claim 44, wherein the sensor is attached to a surface of the coverlet using a bonding method selected from the group consisting of radio frequency welding, ultrasonic welding, and heat sealing.

49. The system of claim 44, wherein the sensor is attached to a surface of the coverlet using an attachment method selected from the group consisting of sewing, hook and loop fasteners, and high friction.

50. The system of claim 44, wherein the passive sensor includes an array of pressure sensing elements.

51. The system of claim 50, wherein the pressure sensing elements include piezoelectric sensors.

52. The system of claim 50, wherein the pressure sensing elements each have two opposite surfaces, each surface being protected by a foam padding.

53. The system of claim 50, wherein the pressure sensing elements are disposed upon a carrier sheet, the carrier sheet being attached to the coverlet.

54. The system of claim 44, wherein the passive sensor includes a sensor array disposed upon a carrier sheet attached to the coverlet.

55. The system of claim 54, wherein the sensor array is attached to a surface of the carrier sheet using adhesive.

56. The system of claim 54, wherein the sensor array includes piezoelectric sensing elements and pressure switches.

57. The system of claim 54, wherein the carrier sheet is formed of a urethane material.

58. The system of claim 54, wherein the carrier sheet is attached to an inner surface of the coverlet.

59. The system of claim 54, wherein the carrier sheet is attached to the coverlet by welding.

60. The system of claim 54, wherein sensors in the sensor array are formed of a polarized polymer film.

61. The system of claim 54, wherein the carrier sheet is detachably connected to the coverlet.

62. The system of claim 54, wherein the carrier sheet is detachably connected to the coverlet with a hook and loop fastener.

63. A system for connection to a mattress to support continuous passive monitoring of a patient, comprising:

a passive sensor for monitoring the patient; and a coverlet configured to substantially surround the mattress;

wherein the sensor is attached to the coverlet and the coverlet is configured to define an opening for inserting the mattress, and wherein a hem surrounds the opening, the hem containing a length of string configured to reduce the size of the opening when the string is tensioned.

64. A system for connection to a mattress to support continuous passive monitoring of a patient, comprising:

a passive sensor for monitoring the patient; and a coverlet configured to substantially surround the mattress;

wherein the sensor is attached to the coverlet and the coverlet is configured to define an opening for inserting the mattress, and wherein straps are arranged to extend across the opening, the straps being configured to reduce the size of the opening when the straps are tensioned.

* * * * *

UNITED STATES PATENT AND TRADEMARK OFFICE
CERTIFICATE OF CORRECTION

PATENT NO. : 7,652,581 B2  Page 1 of 1
APPLICATION NO. : 11/061213
DATED : January 26, 2010
INVENTOR(S) : Gentry et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 372 days.

Signed and Sealed this

Twenty-eighth Day of December, 2010

David J. Kappos
*Director of the United States Patent and Trademark Office*